US008592642B2

(12) United States Patent
Hamase et al.

(10) Patent No.: US 8,592,642 B2
(45) Date of Patent: Nov. 26, 2013

(54) EVALUATION/SCREENING METHOD FOR DISEASES ASSOCIATED WITH D-AMINO ACID UTILIZING DAO1-/-MOUSE

(75) Inventors: Kenji Hamase, Fukuoka (JP); Kiyoshi Zaitsu, Fukuoka (JP); Masashi Mita, Tokyo (JP); Yutaka Ashida, Yokohama (JP); Yousuke Toujo, Yokohama (JP)

(73) Assignees: Kyushu University, National University Corporation, Fukuoka-shi (JP); Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/060,824

(22) PCT Filed: Jul. 31, 2009

(86) PCT No.: PCT/JP2009/063696
§ 371 (c)(1),
(2), (4) Date: May 13, 2011

(87) PCT Pub. No.: WO2010/024091
PCT Pub. Date: Mar. 4, 2010

(65) Prior Publication Data
US 2011/0217707 A1 Sep. 8, 2011

(30) Foreign Application Priority Data
Aug. 26, 2008 (JP) ................................ 2008-217239

(51) Int. Cl.
*G01N 33/00* (2006.01)
*A01K 67/027* (2006.01)
(52) U.S. Cl.
USPC .......................................................... 800/3
(58) Field of Classification Search
USPC .................................................... 800/3, 18
See application file for complete search history.

(56) References Cited

FOREIGN PATENT DOCUMENTS

JP 2009184981 A1 8/2009

OTHER PUBLICATIONS

Hashimoto et al., 2008, Eur. J. Pharmacology, vol. 586, pp. 221-225.*
Morikawa et al.. 2007, Amino Acids, vol. 32, pp. 13-20.*
NCBI printout from web, 1-page.*
Zeleke et al., 2006, Chirality, vol. 18, pp. 544-550.*
Fang et al., 2008, Int. J. Cancer, vol. 122, pp. 1135-1144.*
Carver et al., 2006, Clin. Cancer Res., vol. 12(18) pp. 5305-5311.*
Lutherer et al., 1964, Nature, vol. 201(4916), pp. 303-304.*
Corrigan J.J., D-amino Acids in Animals, Science vol. 164:142-149 (1969).
Hamase, K. et al., D-Amino Acids in Mammals and Their Diagnostic Value, Journal of Chromatography B781: 73-91 (2002).
D'Aniello, A. et al., Occurrence of D-aspartic Acid and N-Methyl-D-aspartic Acid in Rat Neuroendocrine Tissues and Their Role in the Modulation of Luteinizing Hormone and Growth Hormone Release, The FASEB Journal , vol. 14: 699-714 (2000).
Nagata, Y. et al., D-Aspartate Stimulation of Testosterone Synthesis in Rat Leydig Cells, FASEB Letters 444:160-164 (1999).
Nishikawa, T., Metabolism and Functional Roles of Endogenous D-Serine in Mammalian Brains, Biol. Pharm. Bull. 28:1561-1565 (2005).
Fujii, N., D-Amino Acid in Elderly Tissues, Biol. Pharm. Bull. 28:1585-1589 (2005).
Fujii, N. et al., The Presence of D-β-aspartic Acid-Containing Peptides in Elastic Fibers of Sun-Damaged Skin: A Potent Marker for Ultraviolet-Induced Skin Aging, Biochem. Biophys. Res. Commun. 294, 1047-1051 (2002).
Hamase, K., et al., Sensitive Determination of D-Amino Acids in mammals and the Effect of D-Amino-Acid Oxidase Activity on Their Amounts, Biol. Pharm. Bull. 28:1578-1584 (2005).
Konno, R. et al., Mouse Mutant Deficient in D-Amino Acid Oxidase Activity, Genetics 103:277-285 (1983).
Hashimoto, A. et al., Mice Lacking D-Amino Acid Oxidase Activity Disply Market Attenuation of Stereotypy and Ataxia Induced by MK-801, Brain Research, 1033:210-215 (2005).
Hamase, K. et al, Development of Selective Methods for the Determination of Small Amounts of D-Amino Acids in Mammals, Bunseki Kagaku, vol. 53: 677-690 (2004).
Hashimoto, A. et al., Mice Lacking D-Amino Acid Oxidase Activity Exhibit Marked Reduction of Methamphetamine-Induced Stereotypy, European Journal of Pharmacology, vol. 586: 221-225 (2008).
Hamase, K., Sensitive Two-Dimensional Determination of Small Amounts of D-Amino Acids in Mammals and The Study on Their Functions, Chem. Pharm. Bull. (Tokyo). vol. 55: 503-510 (2007).
Sasaki, M. et al., A Single-Base-Pair Substitution Abolishes D-Amino-Acid Oxidase Activity in the Mouse, Biochim. Biophys. Acta., vol. 1139: 315-318 (1992).
Ohgusu, T. et al., High-Throughput Determination of Free D-Aspartic Acid in Mammals by Enzyme Immunoassay Using Specific Monoclonal Antibody, Analytical Biochemistry, vol. 357: 15-20 (2006).
Tojo, Y. et al., Simple and Rapid Genotyping of D-Amino Acid Oxidase Gene Recognizing a Crucial Variant in the ddY Strain Using Microchip Electrophoresis, J. Sep. Sci., vol. 32: 430-436 (2009).
International Search Report dated Sep. 9, 2009, issued for PCT/JP2009/063696 and the English translation thereof.
Extended European Search Report issued in EP 09809745.5, dated Mar. 2, 2012.
M. Saito et al. "Purification of branched-chain amino acid aminotransferase from *Helicobacter pylori* NCTC11637." 10th International Congress on Amino Acids and Proteins—XP-002670046, 2007.
Y. Tojo et al. "Automated and simultaneous two-dimensional micro-high-performance liquid chromatographic determination of proline and hydroxyproline enantiomers in mammals." Journal of Chromatography B, 875 (2008) 174-179.

* cited by examiner

*Primary Examiner* — Peter Paras, Jr.
*Assistant Examiner* — David A Montanari
(74) *Attorney, Agent, or Firm* — Edwards Wildman Palmer LLP

(57) ABSTRACT

Disclosed is an evaluation method which can rapidly discriminate a Dao$^{-/-}$ homozygote from a large number of animals produced in a mating experiment between a DAO enzyme deficient mouse and other disease model mice, to rapidly perform a quantitative measurement of the D-amino acids contained in a large number of samples. The invention provides a method for evaluating the effect of a test condition on a mouse tissue, or cultured tissue cells derived from the tissue. The method comprises the steps of: providing a Dao1$^{-/-}$ mouse or the like; exposing the tissue from the Dao1$^{-/-}$ mouse or the like, to the test condition; and analyzing the effect of exposing the tissue from the Dao1$^{-/-}$ mouse or the like, to the test condition.

12 Claims, 10 Drawing Sheets

FIG.1

```
                    15111
         HpaII      ----------  ----------  ----------  ----------  ----------
      Dao1_cDNA     ----------  ----------  ----------  ----------  ----------
    Dao1_genomic    GAAGCTGGAG  GACAGAGGGG  AGAGGGCACA  GCACAGTCCT  TGCCCCTTCC
   Forward primer   ----------  ------GGG   AGAGGGCACA  GCACAGTC--  ----------
   Reverse primer*  ----------  ----------  ----------  ----------  ----------

15161
         HpaII      ----------  ----------  ----------  ----------  ----------
      Dao1_cDNA     ----------  ----------  ------GTGG  CAAGAGGAGT  GGATGTGATT
    Dao1_genomic    TGTCCCTGAC  TTGTTCTTGC  TGCCAGGTGG  CAAGAGGAGT  GGATGTGATT
   Forward primer   ----------  ----------  ----------  ----------  ----------
   Reverse primer*  ----------  ----------  ----------  ----------  ----------

15211        ↓*          ↓
         HpaII      ----------  CCGG------  --CCGG----  ----------  ----------
      Dao1_cDNA     ATCAACTGCA  CCGGGGTGTG  GGCCGGGGCC  CTGCAAGCAG  ATGCCTCCCT
    Dao1_genomic    ATCAACTGCA  CCGGGGTGTG  GGCCGGGGCC  CTGCAAGCAG  ATGCCTCCCT
   Forward primer   ----------  ----------  ----------  ----------  ----------
   Reverse primer*  ----------  ----------  ----------  ----------  ----------

15261        ↓
         HpaII      --------C   CGG-------  ----------  ----------  ----------
      Dao1_cDNA     GCAGCCAGGC  CGGGGCCAGA  TCATCCAG--  ----------  ----------
    Dao1_genomic    GCAGCCAGGC  CGGGGCCAGA  TCATCCAGGT  GAGGAGACTC  TGTGGTCCAT
   Forward primer   ----------  ----------  ----------  ----------  ----------
   Reverse primer*  ----------  ----------  ----------  ----------  ----------

15311
         HpaII      ----------  ----------  ----------  ----------  ----------
      Dao1_cDNA     ----------  ----------  ----------  ----------  ----------
    Dao1_genomic    GAAGAGCTTG  CCCTGTCTGC  TTGCCCTGTG  CCACTCCAAA  GCTGGTGCCA
   Forward primer   ----------  ----------  ----------  ----------  ----------
   Reverse primer*  ----------  ----------  ----------  ----------  ----------

15361
         HpaII      ----------  ----------  ----------  ----------  ----------
      Dao1_cDNA     ----------  ----------  ----------  ----------  ----------
    Dao1_genomic    CTACAGGGTC  CATGTTGATG  GAGTGACTGC  AGACTTAGAG  GAAGGGACTT
   Forward primer   ----------  ----------  ----------  ----------  ----------
   Reverse primer*  ----------  ----------  ----------  ----------  ----------

15411
         HpaII      ----------  ----------  ----------  ----------  ----------
      Dao1_cDNA     ----------  ----------  ----------  ----------  ----------
    Dao1_genomic    ACTGAAGAAA  TAAGGACCAG  CCTACTCCCT  GCCCTGGTGT  TCTGGGATTT
   Forward primer   ----------  ----------  ----------  ----------  ----------
   Reverse primer*  ----------  ---------G  CCTACTCCCT  GCCCTGGTGT  ----------
```

Dao1_cDNA: 7th exon of mouse Dao1 mRNA
Dao1_genomic: chromosomal DNA near the Dao1$^{G181R}$ mutation
Reverse primer*: corresponding reverse complement
G: A in Dao1$^{G181R}$ mutant
↓*: unable to digest in Dao1$^{G181R}$ mutant

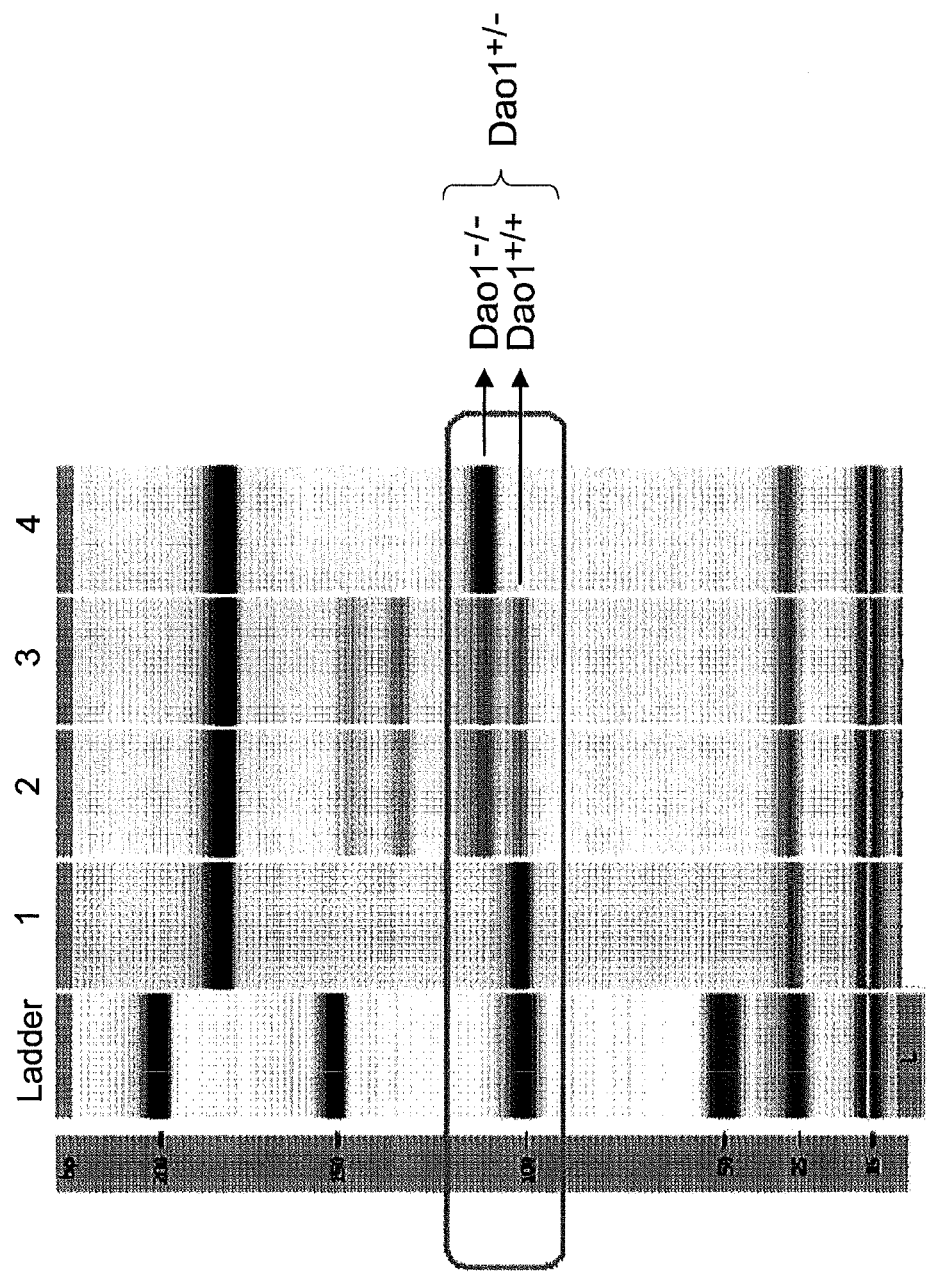

FIG.4-1

| | proline (Pro) | 4-hydroxyproline (Hyp) | |
|---|---|---|---|
| | | *trans* - form | *cis* - form |
| L-enantiomer | L-Pro | trans-L-Hyp | cis-L-Hyp |
| D-enantiomer | D-Pro | trans-D-Hyp | cis-D-Hyp | ddY mouse (*Dao1*[+/+])

ddY mouse (*Dao1*[G181R/G181R])

```
                        SEQUENCE LISTING

<160> NUMBER OF SEQ ID NOS: 5

<210> SEQ ID NO 1
<211> LENGTH: 21
<212> TYPE: DNA
<213> ORGANISM: Artificial
<220> FEATURE:
<223> OTHER INFORMATION: forward primer for detecting Dao1 (G181R)
      mutation

<400> SEQUENCE: 1
gggagagggc acagcacagt c                                             21

<210> SEQ ID NO 2
<211> LENGTH: 21
<212> TYPE: DNA
<213> ORGANISM: Artificial
<220> FEATURE:
<223> OTHER INFORMATION: reverse primer for detecting Dao1 (G181R)
      mutation

<400> SEQUENCE: 2
acaccagggc agggagtagg c                                             21

<210> SEQ ID NO 3
<211> LENGTH: 1712
<212> TYPE: DNA
<213> ORGANISM: Mus musculus
<220> FEATURE:
<221> NAME/KEY: misc_feature
<223> OTHER INFORMATION: cDNA for Dao1 gene
<220> FEATURE:
<221> NAME/KEY: misc_feature
<223> OTHER INFORMATION: wild type cDNA for Dao1 gene

<400> SEQUENCE: 3
attcctggct ggtgggcaga gggctgaagt caacacagcc cagagagtca ggagcagtcc    60
tgctggaacc tgcaccccag gttattttc tcccgacacc tggcaccagt ggctgctgtg   120
atgcgcgtgg ccgtgatcgg agcaggagtc attgggctct ccacagccct ctgcattcat   180
gagcgttacc acccaacaca gccactgcac atgaagatct atgcagatcg attcacccg   240 ttcaccacga gcgatgtggc cgccggcctc tggcagcctt atctctctga ccccagcaac   300
cctcaggagg cggagtggag ccagcaaacg tttgattacc tgctgagctg cctccattct   360
ccaaacgctg aaaaaatggg cctggcccta atctcaggct acaacctctt ccgagatgaa   420
gttccggacc ctttctggaa aaacgcagtt ctgggattcc ggaagctgac ccccagtgag   480
atggacctgt tccctgatta tggctacggc tggttcaata caagcctcct tctagagggg   540
aagagctacc tgccatggct aactgagagg ttaactgaga gggagtgaa gcttatccat   600
```

```
cggaaggtgg agtctctcga agaggtggca agaggagtgg atgtgattat caactgcacc      660
ggggtgtggg ccggggccct gcaagcagat gcctccctgc agccaggccg gggccagatc      720
atccaggtgg aggcccctgc gattaaacac ttcatcctca cccatgatcc tagccttggt      780
atctacaact ctccgtacat catcccaggt tccaagacag ttacgctcgg gggtatattc      840
cagctgggga actggagcgg gttaaacagc gtccgtgacc acaataccat ttggaagagc      900
tgctgtaaac tggagcccac cctgaagaat gcaagaattg tgggtgaact cactggcttc      960
cggccagtcc ggcctcaggt ccggctagaa agagaatggc ttcattttgg atcttcaagt     1020
gcagaggtca tccacaacta tggtcatgga ggttacgggc tcacaatcca ctggggttgt     1080
gcaatggagg cggccaacct cttcgggaaa attctagagg aaaagaagtt gtccaggttg     1140
cctccctccc acctctgagg actctagtga tcaccgtgtg ccccaagacg acacccccc      1200 ttcggccaat gatatgtgat gctcctggat gatgctctct cccagcccc accccagcc      1260 actcccaac ccaccccgac cactccccca gccccgccgg ccactccccc agcccacc       1320 ctggcttcct ctggcaaagg catgaaggga ggaaatcttg ctgctcctgc cactcatcca     1380
ctgctgcctg gtccttccag tgcagtgatt cttgctggtc ctaaccaagg cttgggtgag     1440
ataggctgcg tggtgcaatt cttctcaagc cgtagtgact gtactgaggc tggtggtacc     1500
gggtggcagg acctgcgttc agacctataa ggagtggtct ggatcttttg cttagaactc     1560
tgacgaatgg ttcacaacac actccatgcg tatctgtagt gatgggagga ggggttagg      1620 agcaggacgt tggggagagg aggaggagtt ggaggaggag cactccactg gtcaacatta     1680
ttaaaacact ggatatccaa actcttcagg at                                   1712

<210> SEQ ID NO 4
<211> LENGTH: 350
<212> TYPE: DNA
<213> ORGANISM: Mus musculus
<220> FEATURE:
<221> NAME/KEY: misc_feature
<223> OTHER INFORMATION: wild type chromosome DNA of Dao1 gene
      15111-15460 from transcription start site

<400> SEQUENCE: 4
gaagctggag acagagggg agagggcaca gcacagtcct tgccccttcc tgtccctgac       60
ttgttcttgc tgccaggtgg caagaggagt ggatgtgatt atcaactgca ccggggtgtg     120
ggccggggcc ctgcaagcag atgcctccct gcagccaggc cggggccaga tcatccaggt     180
gaggagactc tgtggtccat gaagagcttg ccctgtctgc ttgccctgtg ccactccaaa     240
gctggtgcca ctacagggtc catgttgatg gagtgactgc agacttagag gaagggactt     300
actgaagaaa taaggaccag cctactccct gccctggtgt tctgggattt                350

<210> SEQ ID NO 5
<211> LENGTH: 21
<212> TYPE: DNA
<213> ORGANISM: Artificial
<220> FEATURE:
<223> OTHER INFORMATION: reverse complement of reverse primer for
      detecting Dao1 (G181R) mutation, Seq Id No.: 2

<400> SEQUENCE: 5
gcctactccc tgccctggtg t                                                21
```

EVALUATION/SCREENING METHOD FOR DISEASES ASSOCIATED WITH D-AMINO ACID UTILIZING DAO1-/-MOUSE

This application is the national phase entry of the international application No. PCT/JP2009/063696 filed Jul. 31, 2009, and claims the right of priority under 35 U.S.C. §365(b) based on Japanese Patent Application No. 2008-217239 filed Aug. 26, 2008, which is hereby incorporated by reference herein in its entirety as if fully set forth herein.

TECHNICAL FIELD

The present invention relates to a method for evaluating of the effect of a test condition on a mouse tissue, or cultured tissue cells derived from the tissue, an evaluation system for carrying out the evaluation method, and a method for screening medicinal and/or cosmetic candidate substances by using the evaluation system.

BACKGROUND ART

All amino acids other than glycine have two optical isomers, referred to as D-type and L-type. The L-amino acids are used in protein synthesis in organisms, and the amino acids contained in proteins are mostly L-amino acids. On the other hand, although D-amino acids are contained in some of the biologically active peptides of lower forms of life, such D-amino acid-containing peptides are often biosynthesized during a process of post-translation modification. That is to say, amino acids, which constitute proteins and peptides, are predominantly L-amino acids, and D-amino acids are an exceptional presence.

D-amino acids are structural constituents of peptide glycans of the cell walls of bacteria. Furthermore, it has been reported that free D-amino acids that do not constitute the peptides are present in lower animals, such as aquatic animals and insects. However, there was a time when it was believed that the amino acids present in higher animals are of the L-type, and that the D-type was present only in trace quantities (Non-Patent Document 1),

[Non-Patent Document 1] Corrigan J. J., Science 164:142-149 (1969).

However, the presence, and the role thereof, of D-amino acids in mammals, including humans, is only just becoming clear in recent years, due to advances in analytical methods such as optical resolution methods (Non-Patent Document 2). In regard to D-aspartate, as a result of double staining methods using an anti-D-aspartate antibody, or the like, it became clear that it is localized in the prolactin producing cells in rat pituitary glands. Furthermore, administration of D-aspartate to cells of a rat pituitary gland-derived cell line that produces and secretes prolactin increases dose-dependently the prolactin secretion. Therefore, it is considered that D-aspartate controls the secretion of prolactin in prolactin producing cells (Non-Patent Document 3).

[Non-Patent Document 2] Hamase K, Morikawa A, and Zaitsu K., J Chromatogr B 781: 73-91 (2002).

[Non-Patent Document 3] D'Aniello A et al., FASEB J 14: 699-714 (2000).

On the other hand, it has been reported that in addition to higher concentrations of D-aspartate constantly being detected in the veins of rat testes compared to in other veinous blood, the synthesis and secretion of testosterone is dose-dependently promoted by providing D-aspartate to Leydig cells isolated and purified from rat testes (Non-Patent Document 4).

[Non-Patent Document 4] Nagata Y et al., FEBS Lett. 444: 160-164 (1999).

It has been reported that D-serine selectively stimulates the glycine binding site of the NMDA receptor, which has been supposed to be associated with schizophrenia, and that neural transmission can be promoted by enhancing the function of glutamate via this receptor (Non-Patent Document 5). It has been reported that schizophrenia is actually improved by the administration of D-serine, and that schizophrenic patients have a lower D-serine concentration in the blood serum compared to healthy individuals.

[Non-Patent Document 5] Nishikawa T, Biol. Pharm. Bull. 28: 1561-1565 (2005).

With regard to the skin science, there is a report in which D-aspartate is present in tissue in which the turnover of proteins does not occur readily, such as in the eye lens (Non-Patent Document 6). Furthermore there is a report that suggests that UV exposure has a strong relationship with D-aspartate formation in the elastic fiber of the skin, since D-aspartate is contained in the elastic fiber of sunburnt skin of elderly subjects but is not contained in the elastic fiber of skin that is not sunburnt (Non-Patent Document 7).

[Non-Patent Document 6] Fujii N et al., Biol. Pharm. Bull, 28: 1585-1589 (2005).

[Non-Patent Document 7] Fujii N. et al., Biochem. Biophys. Res. Commun. 294, 1047-1051 (2002).

However, a large obstacle in exploring the presence and the role of D-amino acids in the mammal, including the human, is that D-amino acids are rapidly degraded. During the degradation of D-amino acids, firstly, the D-amino acid is oxidatively deaminated by a D-amino acid oxidase (EC 1.4.3.3, hereunder referred to as "DAO enzyme"), and is converted to the corresponding α (alpha)-keto acid. Thereafter, the α (alpha)-keto acid is converted to the corresponding L-amino acid by a transaminase. The DAO enzyme is an enzyme that specifically oxidizes D-amino acids, and is expressed in the kidneys, and other organs (Non-Patent Document 8).

[Non-Patent Document 8] Hamase K., Konno R., Morikawa A. and Zaitsu K., Biol. Pharm. Bull, 28: 1578-1584 (2005).

Although the DAO enzyme is encoded by the Dao1 gene of the fifth chromosome in mouse, the missense mutant of this gene was reported in ddY mouse (Non-Patent Document 9). In this mutant gene allele (Dao$^c$ or Dao$^{G181R}$), the Gly residue in position number 181 is substituted by an Arg residue, resulting in a protein that has lost its enzyme activity. Accordingly, the phenotype of the DAO enzyme inactivation is recessively inherited. In an individual of a recessive homozygote (hereunder referred to as a "DAO enzyme deficient mouse"), the blood serum concentration of D-alanine and D-serine rises between 5 to 8 times, and exhibits ataxia and stereotypic behavior (Non-Patent Document 10). There are no reports regarding mating experiments between a DAO enzyme deficient mouse and other disease model mice,

[Non-Patent Document 9] Konno R. and Yasumura Y. Genetics 103: 277-285 (1983).

[Non-Patent Document 10] Hashimoto A., Yoshikawa M., Niwa A. and Konno R., Brain Res. 1033:210-215 (2005).

Problems To Be Solved By The Invention

There is a need to rapidly discriminate a Dao$^{G181R}$/Dao$^{G181R}$ homozygote from a large number of animals produced in a mating experiment between a DAO enzyme deficient mouse and other disease model mice. Furthermore, since the amount of the D-amino acid may be less than approximately 1% of the amount of L-amino acid, there is a need to separate and detect trace quantities of D-amino acids from large quantities of L-amino acids. In addition, there is a need to rapidly perform a quantitative measurement of the D-amino acids contained in samples derived from a large number of individual mice, samples derived from a number of different tissues, and samples exposed to a number of test condition.

DISCLOSURE OF INVENTION

The present invention provides method for evaluating an effect of a test condition on a mouse tissue, or cultured cells derived from the tissue. The method is comprised of the steps of: (1) providing a $Dao1^{+/+}$ mouse and a $Dao1^{-/-}$ mouse; (2) exposing a tissue of the $Dao1^{+/+}$ and $Dao1^{-/-}$ mice, or cultured tissue cells derived from the tissue to the test condition; and (3) analyzing the effect of exposing the tissue or cultured tissue cells derived from the tissue of the Dao1+/+ and $Dao1^{-/-}$ mice to the test condition.

In the method of the present invention, the step 1 may be comprised of discriminating the $Dao1^{+/+}$ mouse and the $Dao1^{-/-}$ mouse according to a method for determining a genotype of $Dao1^{+/+}$, $^{+/-}$ and/or $^{-/-}$, comprising the steps of: identifying a $Dao1^{+/+}$, $^{+/-}$ and/or $^{-/-}$ mouse individually; extracting chromosomal DNA from the mouse; obtaining an amplified DNA fragment by amplifying the region covering the seventh exon of the extracted chromosomal DNA; digesting the amplified DNA fragments with a HpaII restriction enzyme; and analyzing the restriction enzyme-digested products of the amplified DNA fragments.

In the method of the present invention, the step of obtaining the amplified DNA fragments may be comprised of amplifying with oligonucleotide primers consisting of nucleotide sequences recited as SEQ ID NOs: 1 and 2.

In the method of the present invention, the $Dao1^{+/+}$ mouse and the $Dao1^{-/-}$ mouse may share a common combination of alleles for at least one other locus.

In the method of the present invention, the combination of the alleles for the other locus may be comprised of $Hr^{-/-}$.

In the method of the present invention, the step (3) may be comprised of: easuring the D-amino acid content within the tissue or cultured tissue cells derived from the tissue of the $Dao1^{+/+}$ mouse and the $Dao1^{-/-}$ mouse, prior to the step (2); measuring the D-amino acid content within the tissue or cultured tissue cells derived from the tissue of the $Dao1^{+/+}$ mouse and the $Dao1^{+/+}$ mouse, following the step (2) and following exposure to the test condition; and comparing between the D-amino acid content measured prior to the step (2) and the D-amino acid content measured following the step (2).

In the method of the present invention, the D-amino acid content is measured by column chromatography using an optical resolution column system.

In the method of the present invention, the D-amino acid content may be measured by an immunological technique using a monoclonal antibody that discriminates optical isomers.

According to the method of the present invention, the D-amino acid which is evaluated for the effect of the test condition on the mouse tissue or cultured tissue cells derived from the tissue may be D-proline.

In the method of the present invention, the tissue or cultured tissue cell derived from the tissue, for which the D-amino acid content is measured, is derived from one or more tissues selected from a group consisting of epidermis, dermis, kidney, pancreas, testis, adrenal gland, cerebellum, pituitary gland, and blood serum.

In the method of the present invention, the D-amino acid which is evaluated for the effect of the test condition on a mouse tissue or cultured tissue cells derived from the tissue may be D-proline, wherein the D-proline may be measured by column chromatography using an optical resolution column, and the tissue may be epidermis or dermis.

The present invention provides an evaluation system for carrying out the method of the present invention. The evaluation system is comprised of: a $Dao1^{+/+}$ and $Hr^{-/-}$ mouse; a $Dao1^{-/-}$ and $Hr^{-/-}$ mouse; oligonucleotide primers consisting of nucleotide sequences recited as SEQ ID NOs: 1 and 2; and an optical resolution column system that discriminates the optical isomers of proline The present invention provides a method for screening medicinal and/or cosmetic candidate substances that is characterized by evaluating the medicinal and/or cosmetic candidate substances by using the evaluation system of the present invention.

In the present specification, the gene denoted as Dao1 is a mouse gene referred to as D-amino acid oxidase 1, and a detailed explanation is disclosed on the homepage of the Mouse Genome Informatics project at the Jackson Laboratories in the US. As a mutant of the Dao1 gene, Dao1.sup.G181R has been known. In the present invention, the Dao1.sup.−genotype represents any genotype of enzyme activity-deficient mutant allele of D-amino acid oxidase, including, but not limited to, the Dao1.sup.G181R. The Dao1.sup.+genotype of the present invention represents an allele in which, with regard to the D-amino acid oxidase 1 enzyme, is a wild type, that is to say, it is the same, or is substantially the same, as the enzyme in which the amino acid residue at position number 181 of the protein encoded by the Dao1 gene is glycine, and the degradation of the D-amino acid is carried out at the same rate, or substantially the same rate, as the wild type.

The mouse with the $Dao^+$ and $Dao^-$ genotypes in the present invention, may have any allele of other genes. Some of the genes may manifest a specific phenotype in a homozygote, and others may manifest a specific phenotype in a heterozygote. Thus, in the present invention, an evaluation of the effect of the test condition on the D-amino acid content in the mouse tissue or cultured tissue cells derived from the tissue may be performed with a mouse with the $Dao1^{+/+}$ genotype (a $Dao1^{+/+}$ mouse) and a mouse with the $Dao1^{-/-}$ genotype (a $Dao1^{-/-}$ mouse) under a condition in which the combination of the alleles is the same with regard to at least one of the other genes. The effect of the test condition may be the effect of the test condition on the difference of Dao1 action to the phenotype of the first combination of alleles of at least one of the other genes, as compared with Dao1 action to the phenotype of the second combination of alleles of the at least one of the other genes.

In addition to a disease model phenotype, the other genes may be a gene involved in the synthesis of the D-amino acid or the metabolic pathway of degradation, any gene that relates to the health of all organs or the whole body of the mouse such as aging, immunity, stress reactions, nutrition, movement, sensing, memory, behavior, blood circulation, digestion, excretion, reproduction, etc. The other gene may be a causative gene of a disease model mouse that includes, but not limited to, obese mouse ($Lep^{ob}/Lep^{ob}$), thymus dependent immunodeficient mouse ($Foxn1^{nu}/Foxn1^{nu}$), senescence accelerated mouse (SAMP1/TaSlc, SAMP6/TaSlc, SAMP8/TaSlc and/or SAMP10/TaSlc), osteoarthritic mouse ($Laq1^{MRL}/Laq1^{MRL}$), and hairless mouse ($Hr^{hr}/Hr^{hr}$). According to the homepage entitled Online Inheritance of Man of John Hopkins University, the products of the Hr gene are considered to be a transcription factor that is involved in hair formation (http://www.ncbi.nlm.nih.gov/entrez/dispornim.cgi?id=602302). According to the homepage of the Mouse Genome Informatics project, in a mouse, in addition to spontaneous mutants resulting from the insertion of MLV proviruses, such as Hr$^{hr}$, a number of alleles, such as mutants that are accidentally created as a result of the insertion of a transgene, or the like, and knockout mouse, have been reported (http://www.informatics.jax.org/imsr/fetch?page=imsrSummary&op:gsymname=%3D&gsymname=Hr&gsymnameBreadth=C). The Hr$^-$ genotype of the present invention includes Hr$^{hr}$, although it is not limited to this, and represents a genotype in which an adult of an Hr$^{hr}$ homozygote does not have hair as a result of loss of function of any Hr gene product.

In the present invention, when the evaluation of the effect of the test condition on the D-amino acid content is performed under a condition in which the combination of the alleles of at least one of the other genes is same, the step (1) of the method of the present invention, may comprise determining the genotype of at least one of the other genes, in addition to the method for determining the Dao1$^{+/+}$, $^{+/-}$ and/or $^{-/-}$ genotypes.

When the step (1) of the method of the present invention is carried out by selecting by way of the method for determining the Dao1$^{+/+}$, $^{+/-}$ and/or $^{-/-}$ genotypes, the individual identification of the mouse is performed by labeling the breeding cage of the mouse and/or the body of the mouse. Labeling the mouse may involve using ear punching, embedding of a high-frequency or other labeling-purpose chip into the body, or any other method that is well-known to those skilled in the art.

The determination of the Dao1$^{+/+}$, $^{+/-}$ and/or $^{-/-}$ genotypes in the step (1) of the method of the present invention may be performed by any procedure. The determination of the Dao1 genotype is carried out by collecting a small quantity of tissue or other biological material from each individual mouse, and analyzing the Dao1 gene or gene products thereof contained therein. The preferable method for determining the Dao1 genotype is a method that is able to discriminate the Dao1 gene sequence that encodes the amino acid residue of position number 181 of the Dao1 gene product. The chromosomal DNA collection from the individual mouse and the analysis of the Dao1 genotype may be carried out by using any method that is well-known to those skilled in the art. In the analysis of the Dao1 genotype, an amplification method, such as the PCR method, the SMAP method, the LAMP method, or the like, may be used. The different genotypes of the Dao1 gene may be discriminated on the basis of the successful amplification or not with different oligonucleotide primers, in addition to the presence or absence of cleavage site of a specific restriction enzyme on the chromosomal DNA or amplified DNA. The presence or absence of cleavage site of the specific restriction enzyme and/or the presence or absence of amplification may be performed by obtaining an electrophoretic band pattern by the Southern blotting with a probe which can detect the presence or absence of cleavage site of the specific restriction enzyme, following the separation of the amplified DNA, separation of the chromosomal DNA after restriction enzyme digestion, or the like. The preferable method for discriminating the different genotypes of the Dao1 gene is the gene amplification method explained below.

The differentiation of the different genotypes of the Dao1 gene by the gene amplification method in the method for evaluating of the present invention utilizes the fact that the restriction enzyme HpaaII recognizes the mutation site of the Dao1 gene. FIG. 1 is an alignment diagram of the nucleotide sequence related to the method for determining the Dao1 genotype of the present invention. FIG. 1 shows the alignment results of the Dao1 gene chromosomal DNA sequence (Dao1_genomic), a wild type sequence between base number 15111 and base number 15460 from the transcription initiation point of the Dao1 gene (sequence number 4 in the sequence listing), a wild type sequence of cDNA of the 7th exon section that includes a point mutation (the guanine at number 15223 from the transcription initiation point is substituted by adenine) in the Dao1$^{G181R}$ mutant (base number 625 to number 726 of sequence number 3 of the sequence listing), gene amplification-purpose primers (a Forward primer (sequence number 1) and a Reverse primer (sequence number 2)) used in an embodiment of the present invention, and the recognition sequence of the restriction enzyme HpaII. The inverse complementary sequence of the reverse primer sequence (Reverse primer*) is recited as sequence identification number 5 in the sequence listing. FIG. 2 is a HpaII restriction enzyme map of the DNA region used in the method for determining the Dao1 genotype of the present invention. In the 7th exon of the wild type chromosomal DNA, a 3-position HpaII cleavage site (downward facing arrows) is present. Among these, the HpaII recognition sequence (CCGG) nearest the 5' end side becomes CCAG in the Dao1$^{G181R}$ mutant mouse chromosomal DNA, and it is not recognized by HpaII (*). The 7th exon region is amplified by a forward primer (Forward) located in the 6th intron, and a reverse primer (Reverse) positioned in the 7th intron. When the amplification products derived from the wild type mouse genomic DNA (Wild type), and the amplification products derived from the mutant mouse genomic DNA (Dao1$^{G181R}$) are digested by HpaII, they are cleaved in 3 places and 2 places, respectively.

In regard to the measurement of the D-amino acid content in the method for evaluating of the present invention, it is acceptable if it is carried out using any method that is well-known to those skilled in the art. For example, a method in which the D- and L-amino acids are stereospecifically derivatized beforehand by o-phthalaldehyde (OPA), N-tert-butyloxycarbonyl-L-cystine (Boc-L-Cys), or another modifying reagent, and thereafter, performs the separation by using an analytical column such as ODS-80TsQA with a gradient solution of a 100 mM acetate buffer solution (pH 6.0) and an acetonitrile mixed solution, can be used for the simultaneous measurement of the D-type and L-type of aspartate, serine, and alanine. Furthermore, a method in which the D- and L-amino acid is derivatized beforehand by a fluorescence reagent such as 4-fluoro-7-nitro-2,1,3-benzoxydiazole (NBD-F), and thereafter, following stereospecific separation of the amino acids using an analytical column such as ODS-80TsQA, Mightysil RP-18GP, or the like, stereospecifically performs the separation by optical resolution using a Pickle type chiral stationary phase column (for example, Sumichiral OA-2500 S or R), can be used in the microdetermination of proline, leucine, and other amino acids (Kenji Hamase and Kiyoshi Zaitsu, Bunseki Kagaku, Volume 53, 677-690 (2004)). The optical resolution column system in the present specification refers to, at the very least, a separation analysis system using an optical resolution column, and it may include separation analysis by an analytical column other than an optical resolution column. Alternatively, it is possible to determine the quantity of a D-amino acid by an immunological method using a monoclonal antibody that discriminates between the optical isomers of amino acids, for example, a monoclonal antibody that specifically binds to D-leucine, D-aspartate, or the like (Japanese Patent Application No, 2008-27650 Specification).

The test condition in the present invention refer to physical, chemical, and/or biological processing conditions applied systemically or locally to the test animal. The physical processing includes; light rays including ultraviolet rays and infrared rays, or electromagnetic waves, acceleration including sound, vibrations, and zero gravity, temperature, bathing in warm water or cold water, drying, or humidifying, although it is not limited to these. The chemical processing includes protons, and the application of inorganic substances and/or organic substances, although it is not limited to these. The biological processing includes consumption of diet, water, or the like, light-dark cycle, cage area, cage type, the number of individual animals bred in the same cage, other breeding conditions, and administration of medicines, although it is not limited to these. In regard to the test condition in the present invention, these may be one of the aforementioned processes, or a combination thereof, and each process may be carried out continuously and/or intermittently.

In the determination of the D-amino acid content in the method for evaluating of the present invention, "measuring the D-amino acid content within the tissue or cultured tissue cells derived from the tissue of the mouse with the $Dao1^{+/+}$ genotype and the mouse with the $Dao1^{-/-}$ genotype following step (2) and following exposure to the test condition" includes a case where the D-amino acid content is determined following the end of the exposure to the test condition, and a case where the D-amino acid content is determined during the exposure to the test condition.

According to the method for evaluating of the present invention, the effect of the test condition with respect to the various characteristics derived from the tissue of the mouse with the $Dao1^{+/+}$ genotype and the mouse with the $Dao1^{-/-}$ genotype, or cultured tissue cells derived from the tissue, can be evaluated. Such characteristics can be evaluated for the effect of the test condition with respect to: changes in the D-amino acid content; fluctuations in the content of other substances related to the metabolic pathway of the D-amino acid, for example, L-amino acids, α (alpha)-keto acids, or the like; changes in the characteristics related to immunity, including biological and/or pathological characteristics of the digestive system, the liver, the kidneys, the cardiovascular system, or the like, related to the metabolism, digestion and absorption, and degradation and excretion of these substances, as well as allergies with respect to pollen, house dust, and the like, eczema, transplantation immunity of skin and other organs, although it is not limited to these; changes in the characteristics related to the infection by microorganisms or the coexistence with microorganisms; changes in behavior, memory, sensing, and other neurobiological characteristics; changes in the characteristics related to the enhancement and/or suppression of cancers and/or cell proliferation; characteristics related to the aging of skin and other organs, for example, wrinkling, loss of hair, or the like; and characteristics related to the health and/or beauty of skin, such as moisture retention, barrier characteristics, or the like.

BRIEF DESCRIPTION OF THE DRAWINGS

FIG. 1 is an alignment diagram of the nucleotide sequence related to the method for determining the Dao1 genotype of the present invention.

FIG. 3-1 is electrophoretic patterns of the HpaII degradation fragments of the amplification products derived from the chromosomal DNA of a $Dao1^{+/+}$ homozygote mouse (first lane), a $Dao1^{G181R/G181R}$ homozygote mouse (fourth lane), and $Dao^{+/G181R}$ F1 generation heterozygote mice (second and third lane) confirmed from the Dao1 enzyme activity.

FIG. 3-2 is electrophoretic patterns of the HpaII degradation fragments of the amplification products derived from the chromosomal DNA of 12 F2 generation individual mice that are an F2 generation of a cross between a hairless mouse ($Hr^{hr}/Hr^{Hr}$, $Dao1^{+/+}$) and a Dao1 enzyme deficient mouse ($Hr^{+/+}$, $Dao1^{G181R/G181R}$) that possess a hairless phenotype.

FIG. 4-1 are the optical isomers of proline and 4-hydroxyproline.

FIG. 4-2 is a column flow path diagram of a system that simultaneously analyzes the optical isomers of proline and 4-hydroxyproline.

FIG. 6-1 is an elution pattern of an optical resolution column of L-type and D-type proline in the blood serum of a Dao1 gene wild type homozygote mouse ($Dao1^{+/+}$).

FIG. 6-2 is an elution pattern of an optical resolution column of L-type and D-type proline in the blood serum of a Dao1 enzyme activity deficient type homozygote mouse ($Dao1^{G181R/G181R}$).

FIG. 7-1 is a bar graph showing the D-proline abundance in various organs of individuals in which the genotype was determined as $Dao^{+/+}$ and $Dao1^{G181R/G181R}$.

FIG. 7-2 is a bar graph comparing the D-proline abundance in the dermis.

BEST MODE FOR CARRYING OUT THE INVENTION

Hereunder is a detailed description of the present invention. The technical scope of the present invention is limited by the description of the claims, and the embodiments of the present invention are only exemplary.

[Embodiment 1]
Development of a Method for Determining the $Dao1^{+/+}$, $^{+/-}$, and/or $^{-/-}$ Genotypes $Dao1^{G181R}$ is a mutant in which, of the cDNA nucleotide sequence of the Dao1 gene recited as sequence identification number 3, the guanine of number 661 is substituted by adenine. As a result, in contrast to the wild type, in which the cleavage sequence of the restriction enzyme HpaII becomes (C↓CGG), it becomes CCAG in the $Dao1^{G181R}$ mutant and is not cleaved. Here, since the nucleotide numbers 625-726, which includes the site of mutation, includes the 7th exon (GenBank entry number NM_010018.2), it is possible to discriminate between a wild type and a mutant even with chromosomal DNA, according to the presence or absence of the HpaII cleavage site.

Following individual identification of postweaned mice, chromosomal DNA was extracted from the tail of each individual mouse and purified using a commercial mammalian genome DNA mini-prep kit (Sigma, G1N70-1 KT). An oligonucleotide consisting of the nucleotide sequence of sequence number 1 located in the 6th intron was used as the forward primer, and an oligonucleotide consisting of the nucleotide sequence of sequence number 2 located in the 7th intron was used as the reverse primer. The mouse chromosomal DNA was amplified by using a commercial reaction mixture (Promega, M7122) and thermal cycling settings of (1) 94° C., 4 minutes, 1 cycle, (2) 94° C., 30 seconds, 55° C., 30 seconds, 72° C., 30 seconds, 40 cycles, (3) 72° C., 10 minutes, 1 cycle, and (4) 4° C., storage. The PCR reaction products were purified using a commercial kit (Qiagen, 28104), and restriction enzyme processing was performed under the presence of HpaII (TOYOBO, HPA201) and incubated at 37° C. for 3 hours. Following deactivation of the restriction enzyme by heating at 70° C. for 5 minutes, the length of the DNA fragments was analyzed by a commercial electrophoresis microchip (Agilent, 2100 bioanalyzer).

Figure 2:
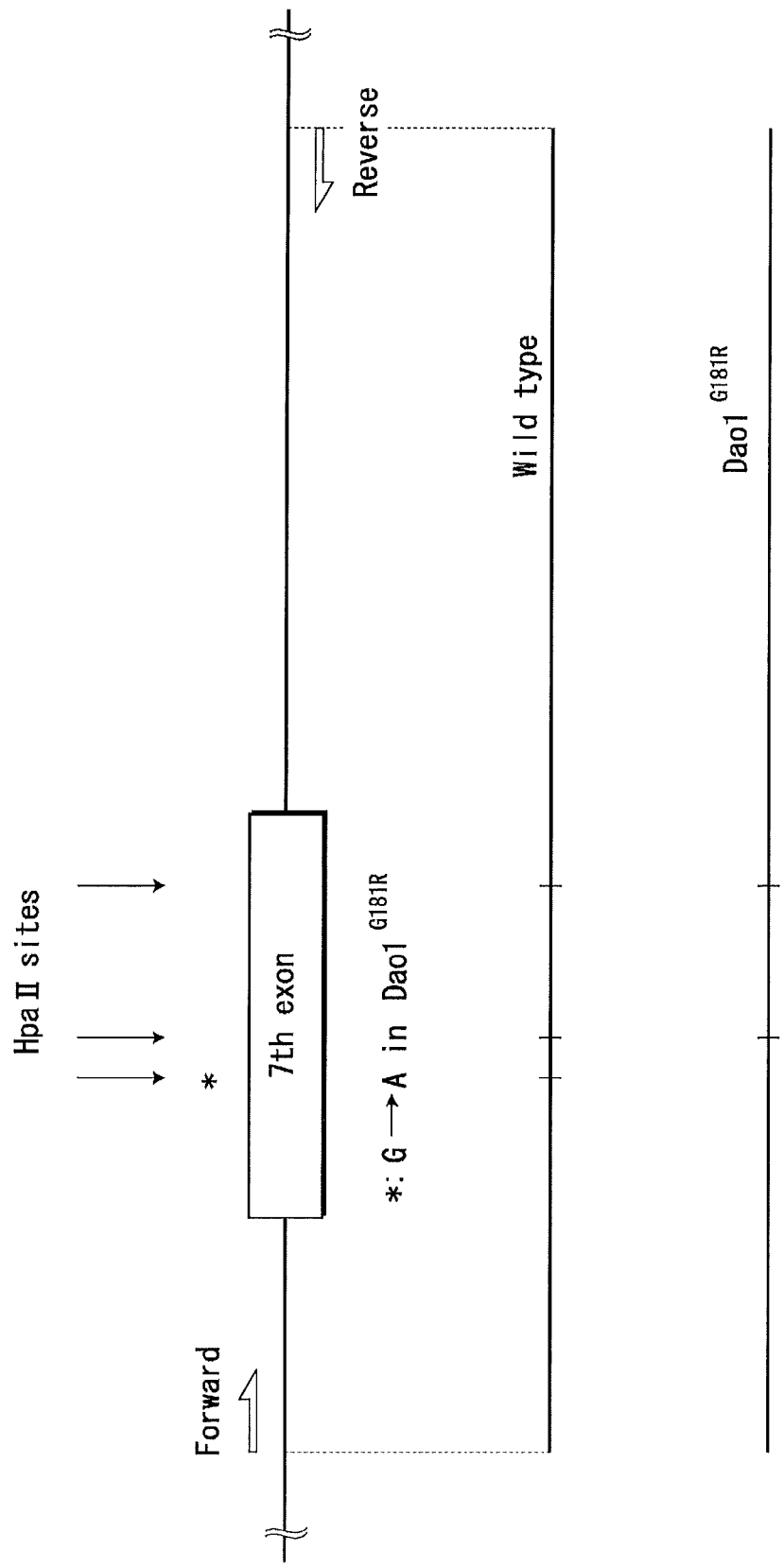
FIG. 2 is a HpaII restriction enzyme map of the DNA region used in the method for determining the Dao1 genotype of the present invention.
Figures 2, 3:
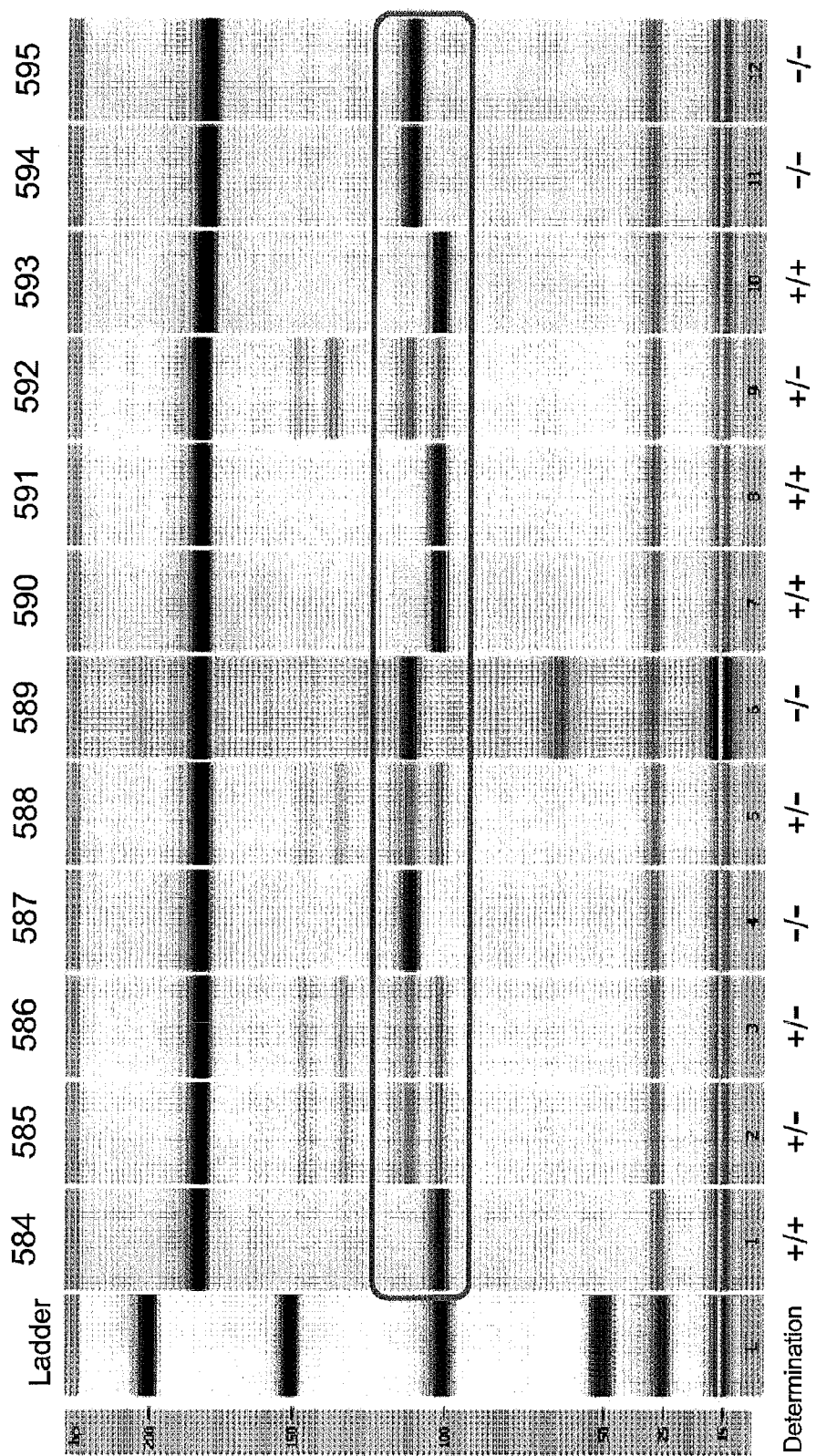
Figures 1, 6:
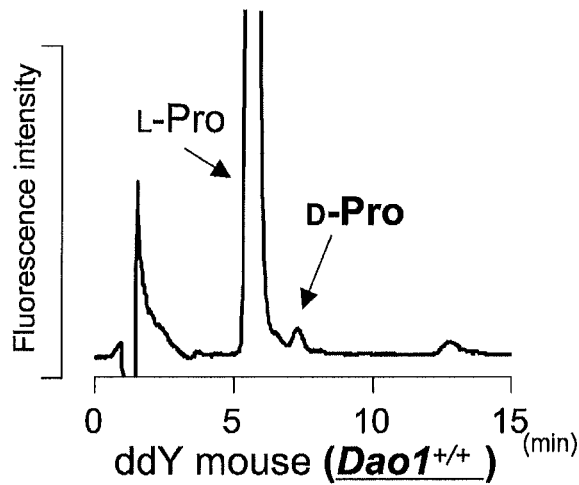
Figures 2, 6:
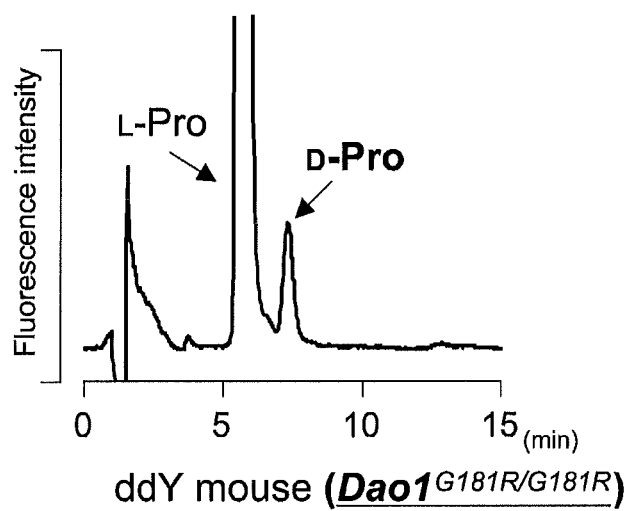

FIG. 3-1 is an electrophoretic pattern of the HpaII degradation fragments of the amplification products derived from the chromosomal DNA of a Dao1$^{+/+}$ homozygote mouse (first lane), a Dao1$^{G181R/G181R}$ homozygote mouse (fourth lane), and Dao$^{+/G181R}$ F1 generation heterozygote mice (second and third lane) confirmed from the Dao1 enzyme activity. As can be understood from FIG. 3-1, since a DNA fragment of 95 bp can be obtained from the chromosomal DNA of the Dao1$^{+}$ gene, and a DNA fragment of 107 bp can be obtained from the chromosomal DNA of the Dao1$^{G181R}$ gene, a wild type homozygote, and a mutant homozygote and heterozygote were able to be clearly discriminated. FIG. 3-2 is the result of performing the Dao1 gene determination on 12 F2 generation individual mice that are an F2 generation of a cross between a hairless mouse (Hr$^{hr}$/Hr$^{Hr}$, Dao1$^{+/+}$) and a Dao1 enzyme deficient mouse (Hr$^{+/+}$, Dao1$^{G181R/G181R}$), which possess a hairless phenotype. Table 1 is a table in which the Dao1 genotype and sex of 138 F2 generation individual mice, which possess a hairless phenotype, have been compiled.

TABLE 1

| F2 Generation Hairless Mouse (Hr$^{-/-}$) | | | | | |
|---|---|---|---|---|---|
| Dao1$^{+/+}$ 39 | | Dao1$^{+/-}$ 55 | | Dao1$^{-/-}$ 44 | |
| F | M | F | M | F | M |
| 18 | 21 | 31 | 24 | 22 | 22 |

F is female, and
M is male.

As discussed above, as a result of the present determination method, it became possible to rapidly determine the Dao1 genotype of a large number of individual mice.

[Embodiment 2]
Development of a Method for Quantitative Analysis of the Optical Isomers of Proline and 4-Hydroxyproline Proline and 4-hydroxyproline are high in content in skin collagen. Therefore, a method that can simultaneously separate and quantitatively analyze all of the optical isomers of both proline and 4-hydroxyproline was developed.

Figures 2, 4:
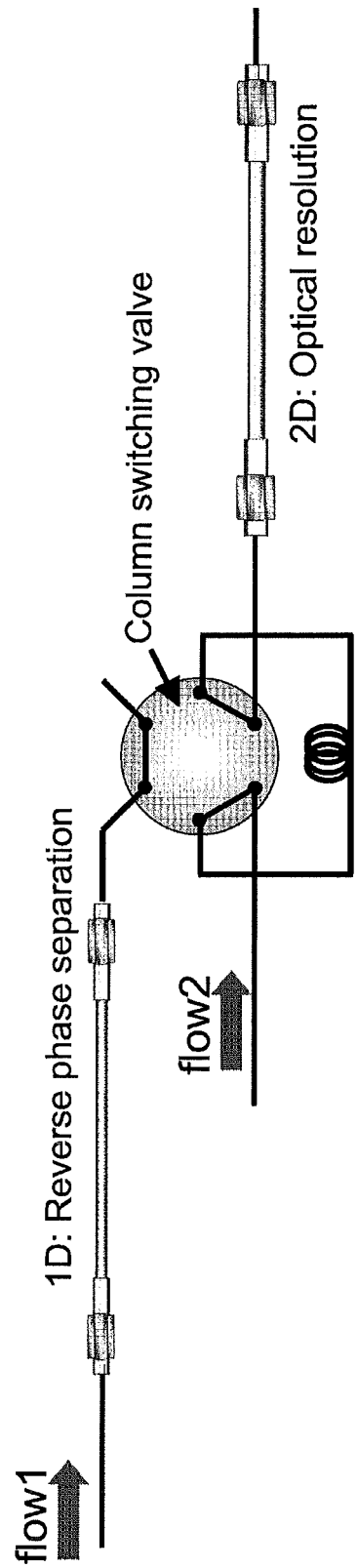

FIG. 4-1 shows the optical isomers of proline and 4-hydroxyproline. Although there are just 2 types of optical isomers, the L-type or D-type, for proline, in regard to the optical isomers of 4-hydroxyproline, there are 4 types as a result of the difference in the trans-type and the cis-type in addition to the difference in the L-type or the D-type. Firstly, fluorescence labeling was performed by derivatizing the amino acid with a fluorescence reagent NBD-F. Thereafter, as shown in FIG. 4-2, reverse phase separation chromatography was performed in a first column, and the respective peaks for trans-4-hydroxyproline, cis-4-hydroxyproline, and proline were detected. Then, the fractions of the respective peaks were divided using a column switching valve, introduced into a second column, and optical resolution chromatography was performed.

Figure 5:
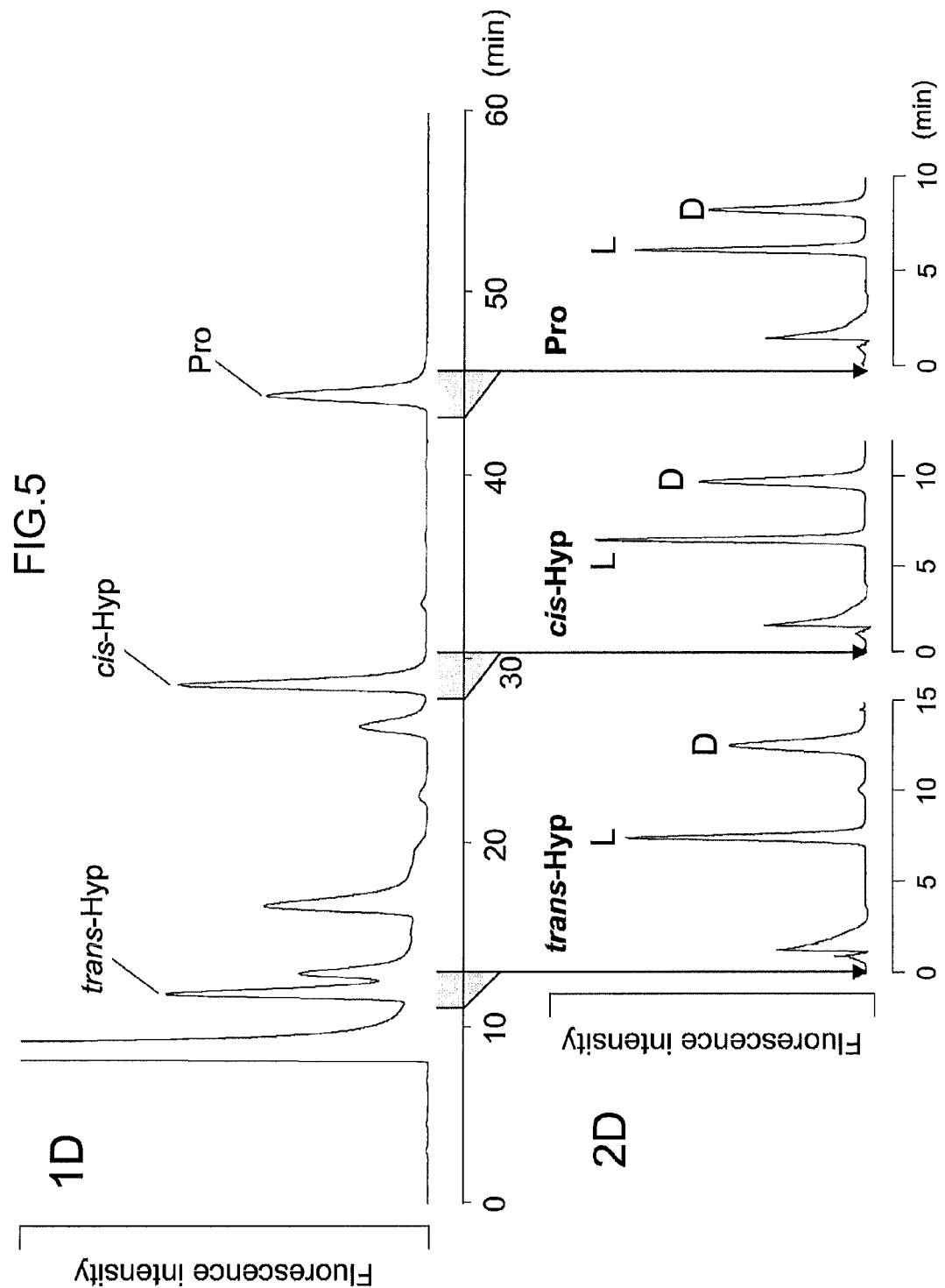
FIG. 5 are waveform diagrams (D1 and D2) of the elution pattern of the first and the second columns of the system that simultaneously analyzes the optical isomers of proline and 4-hydroxyproline.

The waveform diagram 1D of FIG. 5 is one that was detected at a fluorescence emission of 530 nm by irradiating the elution pattern of a monolithic ODS column using a solvent with a flow rate of 40 μ(micro) L/min with an excitation light of 470 nm. The waveform diagram 2D is the result of automatically detecting the respective peaks of trans-4-hydroxyproline, cis-4-hydroxyproline, and proline of the elution pattern of 1D, and performing optical resolution chromatography by performing valve switching and introducing only the fractions of the respective peaks to a QN-2-AX column.

The waveform diagram of FIG. 6-1 is an elution pattern of an optical resolution column of L-type and D-type proline in the blood serum of a Dao1 gene wild type homozygote mouse (Dao1$^{+/+}$), and the waveform diagram of FIG. 6-2 is an elution pattern of an optical resolution column of L-type and D-type proline in the blood serum of a Dao1 enzyme activity deficient type homozygote mouse (Dao1$^{G181R/G181R}$). Although D-proline could be barely detected in a Dao1 wild type homozygote mouse, it could be clearly detected in a Dao1 enzyme activity deficient type homozygote mouse.

Figures 1, 7:
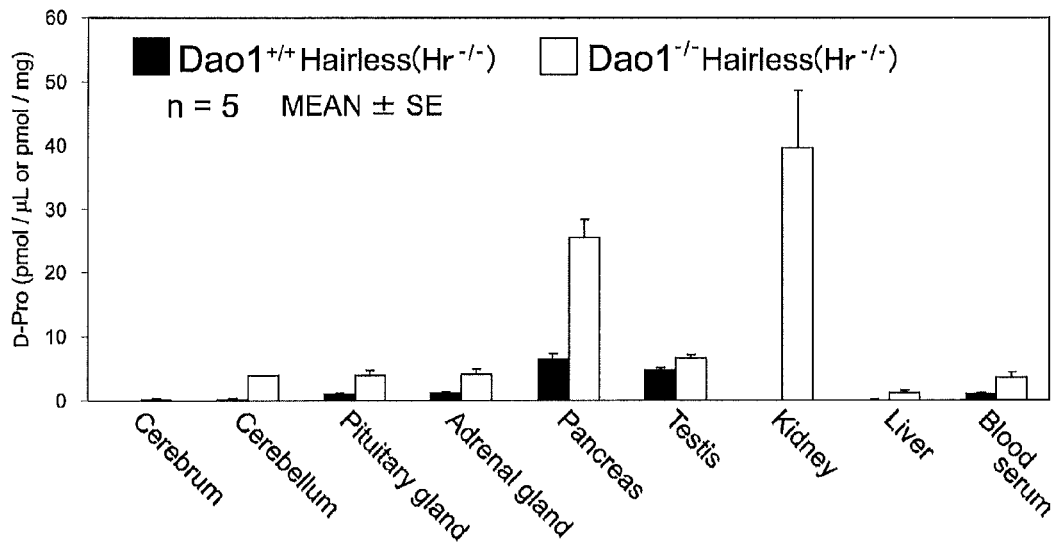
Figures 2, 7:
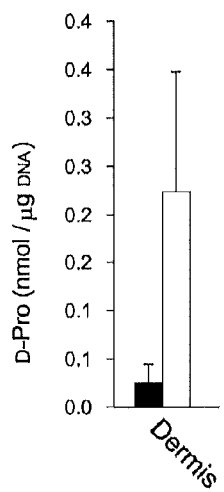

FIG. 7-1 is the result of comparing the D-proline abundance in various organs of individuals for which the genotypes were determined as Dao1$^{+/+}$ and Dao1$^{G181R/G181R}$ among F2 generation hairless mice of a cross between a hairless mouse and a Dao1 enzyme activity deficient type mouse as determined in Embodiment 1, and FIG. 7-2 is the result of comparing the D-proline abundance in the dermis. The units of the vertical axis of the graph of FIG. 7-1 are pmol/μ (micro) L with respect to the blood serum, and pmol/mg in other tissue. The units of the vertical axis of the graph of FIG. 7-2 are nmol/μ (micro) g DNA. In both, the average and standard error of the measured quantity in the mouse organs for the 5 respective mice are displayed. In addition to the blood serum, several times or more D-proline was present in the Dao1 enzyme activity deficient mouse than the wild type mouse in the pituitary gland, adrenal gland, pancreas, and dermis. Furthermore, although D-proline was barely detected in the cerebellum, kidneys, and liver of a Dao1 enzyme activity wild type mouse, D-proline was clearly detected in a Dao1 enzyme activity deficient mouse. The D-proline quantity in the testis of a Dao1 enzyme activity deficient mouse is just slightly more than in a wild type mouse, and a marked difference was not observed. Also, in regard to the skin, it has become clear for the first time that the D-amino acid content in a Dao1 enzyme activity deficient mouse is greater than in a wild type. Hereafter, the effect of ultraviolet light irradiation and aging on the D-amino acid content in the skin will be made clear. In this analysis, with regard to the content of D-4-hydroxyproline, both the cis-isomer and the trans-isomer were below the detection limit in all tissues.

[Embodiment 3]
Tumor Growth in Dao1 Enzyme Deficient Mouse

Sarcoma cells of the Swiss Webster Sarcoma 180 line were cultured using a 10% fetal bovine serum (Irvine Scientific, Lot #300A80601) added DMEM (Sigma) medium under humidified conditions with 5% $CO_2$ at 37° C. A suspension of $1 \times 10^7$ cells/mL was prepared, and 0.05 mL each of the footpad of the right hind leg of a Dao1 enzyme deficient mouse or a wild type mouse were transplanted by endermic injection. The major axis, minor axis, and thickness of the tumor was measured with a caliper every week following the transplant, and the tumor volume was calculated by the formula below.

Tumor volume (mm$^3$)=major axis (mm)×minor axis (mm)×(thickness (mm)−3)

Here, in regard to the thickness, the original thickness of the foot was made 3 mm, and the difference thereof was made the thickness of the foot.

Figure 8:
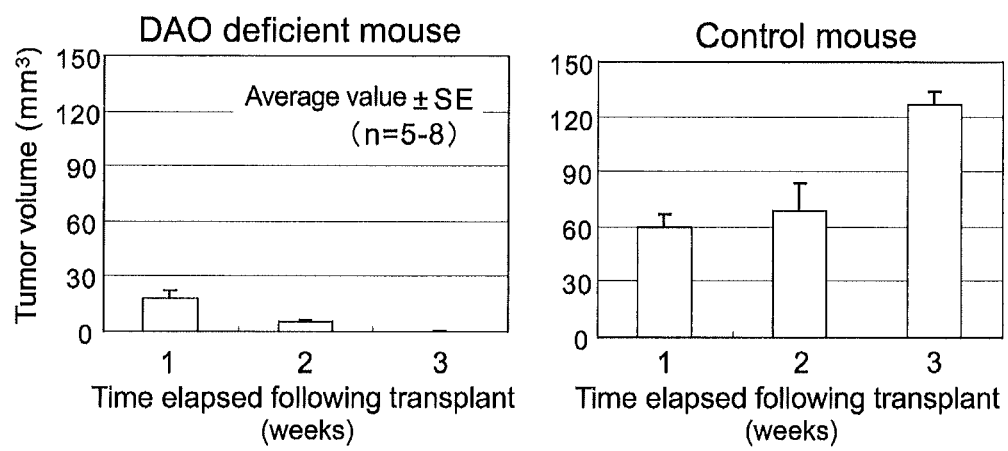
FIG. 8 is a bar graph examining the growth of tumor cells in Dao1 enzyme deficient mice.

The result is shown in FIG. 8. FIG. 8 is a bar graph comparing the change in the tumor volume for a Dao1 enzyme deficient mouse and a control mouse after 1, 2, and 3 weeks elapsed following the transplant. In contrast to the control mouse, in which a tumor volume that was already 60 mm$^3$ 1 week after the transplant increased 2-fold in 3 weeks, in the Dao1 enzyme deficient mouse, the tumor volume, which was only approximately 20 mm$^3$ 1 week after the transplant, decreased to approximately 5 mm$^3$ at 2 weeks, and was completely eliminated at 3 weeks. From this result, it became clear that in a Dao1 enzyme deficient mouse, there is activity that suppresses the growth of the transplanted tumor and eliminates the tumor.

The crossing experiment system established this time between a hairless mouse and a Dao1 enzyme deficient mouse is anticipated to be greatly utilized hereafter for elucidating the role performed by D-amino acids with respect to collagen diseases or collagen disease-related diseases, such as erythematodes, skin bound disease, dermatomyositis, Sjoegren syndrome, polyarteritis nodosum, Bechet's disease, rheumatoid arthritis, or the like, diabetes, photodermatitis, contact dermatitis, decubitus ulcers, and dermal observations such as stains, subfuse, wrinkling, sagging, or the like.

The invention claimed is:

1. A method for evaluating an effect of a transplanted tumor on a mouse tissue, or cultured cells derived from the tissue, said method comprising the steps of:
   (1) providing a Dao $1^{+/+}$ mouse and a Dao $1^{-/-}$ mouse,
   (2) exposing a tissue of the Dao $1^{+/+}$ and Dao $1^{-/-}$ mice, or cultured tissue cells derived from the tissue to the transplanted tumor, and
   (3) comparing changes detected in the tissue or cultured tissue cells derived from the tissue of the Dao $1^{+/+}$ and Dao $1^{-/-}$ mice exposed to the transplanted tumor with tissue or cultured tissue cells derived from the tissue of the Dao $1^{+/+}$ and Dao $1^{-/-}$ mice that were not exposed to the transplanted tumor, wherein the mice of step (1) are provided by the following steps:
   (a) identifying a Dao $1^{+/+}$, $^{+/-}$ and/or $^{-/-}$ mouse individually,
   (b) extracting chromosomal DNA from the mouse (a),
   (c) obtaining an amplified DNA fragment by amplifying the region covering the seventh exon of the Dao 1 gene from the extracted chromosomal DNA,
   (d) digesting the amplified DNA fragment with a HpaII restriction enzyme and examining whether the amplified DNA fragment is cleaved or not,
   (e) determining a genotype of Dao $1^{+/+}$, $^{+/-}$ and/or $^{-/-}$; and
   (f) discriminating the Dao $1^{+/+}$ mouse from the Dao$^{-/-}$ mouse.

2. The method according to claim 1, wherein said step of obtaining the amplified DNA fragments is comprised of amplifying with oligonucleotide primers consisting of nucleotide sequences recited as SEQ ID NOs: 1 and 2.

3. The method according to claim 1, wherein the Dao$1^{+/+}$ mouse and the Dao$1^{-/-}$ mouse share a common combination of alleles for at least one other locus.

4. The method according to claim 3, wherein the combination of the alleles for the other locus is comprised of Hr$^{-/-}$.

5. The method according to claim 4, wherein step (3) is comprised of: measuring the D-amino acid content within the tissue or cultured tissue cells derived from the tissue of the Dao$1^{+/+}$ mouse and the Dao$1^{-/-}$ mouse, prior to step (2);
   measuring the D-amino acid content within the tissue or cultured tissue cells derived from the tissue of the Dao$1^{+/+}$ mouse and the Dao$1^{-/-}$ mouse, following step (2) and following exposure to the transplanted tumor; and comparing between the D-amino acid content measured prior to step (2) and the D-amino acid content measured following step (2).

6. The method according to claim 5, wherein the D-amino acid content is measured by column chromatography using an optical resolution column system.

7. The method according to claim 5, wherein the D-amino acid content is measured by an immunological technique using a monoclonal antibody that discriminates optical isomers.

8. The method according to claim 5, wherein the D-amino acid is D-proline.

9. The method according to claim 5, wherein the tissue or cultured tissue cell derived from the tissue, for which the D-amino acid content is measured, is derived from one or more tissue selected from a group consisting of epidermis, dermis, kidney, pancreas, testis, adrenal gland, cerebellum, pituitary gland, and blood serum.

10. The method according to claim 9, wherein the D-amino acid is D-proline, the D-proline is measured by column chromatography using an optical resolution column, and the tissue is epidermis or dermis.

11. An evaluation system for carrying out the method of claim 10 comprising:
    (1) a Dao$1^{+/+}$/Hr$^{-/-}$ mouse and a Dao$1^{-/-}$/Hr$^{-/-}$ mouse,
    (2) oligonucleotide primers consisting of nucleotide sequences set forth in SEQ ID NOs: 1 and 2; and
    (3) an optical resolution column system that discriminates the optical isomers of proline.

12. The method according to claim 1, wherein the tumor is derived from the Swiss Webster Sarcoma 180 line.

* * * * *